United States Patent [19]
Goldenberg

[11] Patent Number: 5,776,093
[45] Date of Patent: Jul. 7, 1998

[54] METHOD FOR IMAGING AND TREATING ORGANS AND TISSUES

[75] Inventor: Milton David Goldenberg, Short Hills, N.J.

[73] Assignee: Immunomedics, Inc., Morris Plains, N.J.

[21] Appl. No.: 866,789

[22] Filed: Apr. 7, 1992

Related U.S. Application Data

[63] Continuation-in-part of Ser. No. 167,077, Mar. 11, 1988, Pat. No. 5,101,827, which is a continuation of Ser. No. 751,877, Jul. 5, 1985, Pat. No. 4,735,210.

[51] Int. Cl.$^6$ ............................ A61N 1/30; A61K 35/14
[52] U.S. Cl. ...................... 604/20; 600/420; 530/388.2; 530/391.3; 424/1.49
[58] Field of Search ................ 128/653.1, 653.2, 128/653.4, 654; 436/806; 424/4, 7, 1.1, 1.49; 358/111; 324/307, 310; 604/20, 28, 49; 530/388.2, 389.8, 391.3; 600/410, 411, 420

[56] References Cited

U.S. PATENT DOCUMENTS

| 3,927,193 | 12/1975 | Hansen et al. | 424/1.1 |
| 4,036,945 | 7/1977 | Haber. | |
| 4,331,647 | 5/1982 | Goldenberg | 424/1.1 |
| 4,361,544 | 11/1982 | Goldenberg | 424/1.1 |
| 4,732,864 | 3/1988 | Tolman. | |
| 4,859,449 | 8/1989 | Mattes. | |

*Primary Examiner*—Michael Buiz
*Assistant Examiner*—A. T. Nguyen
*Attorney, Agent, or Firm*—Foley & Lardner

[57] ABSTRACT

Provided are methods and compositions for detecting and treating normal, hypoplastic, ectopic or remnant tissue, organ or cells in a mammal. The method comprises parenterally injecting a mammalian subject, at a locus and by a route providing access to said tissue or organ, with an composition comprising antibody/fragment which specifically binds to targeted organ, tissue or cell. The antibody/fragment may be administered alone, or labeled or conjugated with an imaging, therapeutic, cytoprotective or activating agent.

14 Claims, No Drawings

METHOD FOR IMAGING AND TREATING ORGANS AND TISSUES

RELATIONSHIP TO OTHER APPLICATIONS

This application is a continuation in part of U.S. Ser. No. 167,077, filed Mar. 11, 1988, now U.S. Pat. No. 5,101,827, which in turn is a continuation of U.S. Ser. No. 751,877, filed Jul. 5, 1985, now U.S. Pat. No. 4,735,210, issued Apr. 5, 1988.

BACKGROUND OF THE INVENTION

1. Field of the Invention

The present invention relates to methods for imaging and treating hypoplastic, absent, anatomically displaced or ectopic tissues and organs and to a kit suitable for use therefor.

The invention also relates to methods for detecting the condition of adjacent organs and detecting tissue retained after surgical removal of an organ.

The invention also relates to methods of treating and ablating hypoplastic and ectopic tissues or normal tissues.

The invention also relates to methods for protecting normal tissue during radiation or chemotherapy of cancer, and composition and kits useful in the method.

2. Description of the Prior Art

There is a need for a method that clearly delineates hypoplastic, absent, anatomically displaced or ectopic tissue or organs and for a method for treating conditions involving such tissues or organs.

It is important in certain clinical situations to detect the presence or absence of particular tissues or organs. Moreover, it is often necessary to determine whether an organ is anatomically correct and whether it has pathology by a non-invasive technique. It would be desirable to have an organ imaging method using organ-specific imaging agents that would make it possible to obtain a "positive" image of the organ, when normal, and a defect in organ visualization if pathology is present. Such a method would provide a new approach to scintigraphic and magnetic resonance imaging of organs and tissues in the body based upon their immunological specificity.

Normal tissues and organs have been imaged by magnetic resonance imaging techniques, but not with the use of imaging-enhancing contrast agents, and not with antibody-conjugated imaging agents.

Methods of imaging tumors and infectious lesions using labeled antibodies and antibody fragments which specifically bind markers produced by or associated with tumors or infectious lesions have been disclosed, inter alia, in Hansen et al., U.S. Pat. No. 3,927,193 and Goldenberg, U.S. Pat. Nos. 4,331,647, 4,348,376, 4,361,544, 4,468,457, 4,444,744, 4,460,459 and 4,460,561, and in related pending applications U.S. Ser. Nos. 609, 607 and 633,999, the disclosures of all of which are incorporated herein in their entireties by reference. See also DeLand et al., J. Nucl. Med., 20, 1243–50(1979).

These methods use radiolabeled antibodies which specifically bind to markers produced by or associated with tumors or infectious lesions, and result in a "positive" image, i.e., uptake of radioactivity attached to the antibody in the structure involved with tumor or infectious lesion and having the appropriate antibody target, thus permitting a visualization of the involved structure. Further improvements in the specificity and resolution of these methods is achieved by the use of various substraction techniques which are also disclosed in the aforementioned references, and which enable background, non-specific radioactivity to be distinguished from specific uptake by the tumor or lesion.

Antibody conjugates comprising organ-specific and tissue-specific antibodies and addends for scintigraphic detection or magnetic resonance image enhancement have not been used as organ imaging reagents.

A need continues to exist for imaging and therapeutic methods which are more sensitive and specific and for organ imaging and therapeutic reagents and methods with high specificity for differentiation of particular organs and tissues from surrounding structures.

OBJECTS OF THE INVENTION

One object of the present invention is to provide a method for obtaining scintigraphic images that permits higher resolution and greater specificity for hypoplastic, absent, anatomically displaced or ectopic tissues and organs.

Another object of the invention is to provide organ- and tissue-specific methods and agents for scintigraphic and magnetic resonance imaging.

Another object of the invention is to provide reagents and kits suitable for use in the imaging methods of the invention.

Another object of the invention is to provide methods for detecting the condition of adjacent organs and detecting tissue retained after surgical removal of an organ.

Another object of the invention is to provide methods and agents for treatment of normal organs and tissues that are hypoplastic, remnants, or anatomically displaced.

Another object of the invention is to provide methods and agents for ablating normal cells and tissues as part of a therapeutic intervention.

Another object of the invention is to provide methods for protecting normal tissue during radiation or chemotherapy of cancer, and composition and kits useful in the method.

Another object of the invention is to provide methods for altering the functions of a cell or tissue, especially hormone end organs.

Upon further study of the specification and appended claims, further objects and advantages of this invention will become apparent to those skilled in the art.

SUMMARY OF THE INVENTION

In one embodiment, the invention provides an imaging method for positive imaging of an hypoplastic, absent, anatomically displaced or ectopic tissue or organ in a mammal. The method comprises the steps of (a) parenterally injecting a mammalian subject, at a locus and by a route providing access to said tissue or organ, with an amount of a scintigraphic imaging agent or magnetic resonance image enhancing agent sufficient to permit a scintigraphic image or an enhanced magnetic resonance image of said structure to be effected; and (b) obtaining a scintigraphic image or an enhanced magnetic resonance image of said structure, at a time after injection of said agent sufficient for said agent to accrete in said structure. The imaging agent comprises an antibody/fragment which specifically binds to said organ or tissue, and which is labeled with a radioisotope or a magnetic resonance enhancing agent.

In another embodiment, the invention provides a method for treating hypoplastic, ectopic or remnant tissue or organ in a mammal. The method comprises parenterally injecting a mammalian subject, at a locus and by a route providing access to said tissue or organ, with a pharmaceutically effective amount of an antibody/fragment which specifically binds to said organ or tissue. The antibody/fragment is conjugated with a therapeutic agent.

In another embodiment, the invention provides a method for detecting organ tissue retained after surgical removal of a portion of the organ, wherein the organ tissue produces or is associated with a marker substance. The method comprises injecting a human subject parenterally with an antibody specific to the marker substance and radiolabeled with a pharmacologically inert radioisotope capable of detection using a photoscanning device.

In another embodiment, the invention provides a method for determining in a mammal, a first organ's condition and integrity, the first organ producing or being associated with a marker substance and being adjacent to a second organ which has been surgically removed from the mammal. The method comprises injecting the mammal parenterally with an antibody specific to the marker substance and radiolabeled with a pharmacologically inert radioisotope capable of detection using a photoscanning device.

In another embodiment, the invention provides a method for treating hypoplastic or ectopic tissue which produces or is associated with a marker substance. The method comprises injecting a human subject parenterally with an antibody specific to the marker substance and conjugated with a cytotoxic agent.

In another embodiment, the invention provides a method for destroying bone-marrow cells in a patient prior to regrafting with normal bone marrow cells. The method comprises treating the patient with a cytotoxic amount of an antibody or antibody fragment specific to a marker associated with or produced by bone marrow cells and which is conjugated to a cytotoxic agent.

In another embodiment, the invention provides an improved method of therapy of cancer, wherein a human patient suffering from a cancer susceptible to treatment with radiation or a cytotoxic agent is treated with a therapeutic amount of radiation or a cytoxic agent. The improvement comprises administering to the patient a cytotoxic-protective agent conjugated to an antibody or antibody fragment which specifically binds to an antigen which is produced by or associated with a normal cell.

In another embodiment, the invention provides a method of affecting a function of a non-malignant cell in a mammalian subject, the method comprising administering to the subject a composition comprising an antibody specific to a growth factor receptor or hormone receptor on the targeted cell, wherein the antibody affects the function and proliferation of the cell.

In another embodiment, the invention provides a method of treating a condition affecting non-malignant cells in a mammalian subject, the method comprising administering to a subject requiring such treatment, a composition comprising an antibody or fragment specific to a hormone receptor or growth factor on a targeted cell, wherein the antibody or fragment is conjugated to a therapeutic agent.

In another embodiment, the invention provides an immunological method of affecting a hormonal function of a cell in a mammalian subject, the method comprising administering to the subject a composition comprising an antibody or fragment specific to a hormone receptor on a targeted cell, wherein the antibody or fragment affects the hormonal function of the targeted cell.

In another embodiment, the invention provides an immunological method of ablating a cell in a mammalian subject, the method comprising administering to the subject requiring ablation of cell, a composition comprising an antibody or fragment specific to a hormone receptor or growth factor receptor on a cell targeted for ablation, wherein the antibody or fragment is conjugated to a chemical or radiation ablation agent.

Compositions and reagents and kits useful for practicing the methods of the invention are also provided.

DETAILED DESCRIPTION OF THE INVENTION

The above methods are beneficial for imaging and/or, where appropriate, treatment, (1) hypoplastic or absent tissue or organs, in conditions such as, juvenile diabetes, wherein the islet cells of the pancreas can be atrophic or significantly reduced; thymic aplasia or agenesis; DiGeorge's Syndrome wherein there is a hypoplasia or absence of parathyroid and the thymus, (2) ectopic tissue and organs, such as, implants of endometrial glands and stroma, (3) retained tissue, such as, retained placental tissue after pregnancy, and organ remnants after surgical removal of the organ, and (4) the condition of organs adjacent to a surgically removed organ.

(5) ablation of certain normal organs and tissues for other therapeutic purposes, such as the spleen in patients with immune disease or lymphomas, the bone marrow in patients requiring bone marrow transplantation, or normal cell types involved in pathological processes, such as certain T-lymphocytes in particular immune diseases.

The above methods include the use of a growth factor receptor antibody or a hormone receptor antibody to target to end-organs bearing such receptor(s), the functions of which can be blocked with said antibodies. An isotopic or drug conjugate of these antibodies can also be used to deliver a therapeutic agent to said tissues and organs, in order to affect diseases of tissues which bear such receptors. For example, in endometriosis, involving ectopic endometrial tissue, the current standard drug therapy involves administration of a synthetic steroid derived from ethisterone (DANOCRINE brand of danazol), which is chemically a 17-alpha-Pregna-2,3-dien-20-yno]2,3,3-d]-isoxazol-17-ol. This probably acts, at least in part, on sex steroid metabolism and with sex hormone receptors, particularly follicle-stimulating hormone (FSH) and luteinizing hormone (LH) at the target organ. It is now possible to use an antibody against these gonadal steroid receptors, alone or as an immunoconjugate with isotopes, drugs, toxins, hormone antagonists, cytokines, autocrines, etc., to inactivate and make the ectopic endometrium atrophic.

The above methods include providing an immunological method of affecting ovarian and other hormone end-organ function, such as to induce amenorrhea or sterility. By use of an ovarian-targeting antibody or an antibody to an ovarian-related hormone receptor, such as FSH receptor, either as unconjugated antibodies or as antibodies conjugated with a therapeutic principle, a relatively convenient and safe method of blocking ovarian function and inducing atrophy at the end-organ can be achieved.

Many hormone and growth factor receptors are known, and frequently show sufficient organ and tissue proclivity to allow these to serve as targets for antibodies which, when bound to said receptors, affect the function of the tissues and result in an immunological or, by the use of conjugates with drugs, a chemical ablation, or a radiation ablation when used as a conjugate with therapeutic isotopes.

Another application is in the treatment of fibrocystic breast disease. An antibody to FSH receptor or to estrogen receptor can be given alone or as an immunoconjugate with a therapeutic principle to decrease the fibrocystic disease and to control its symptoms.

Still another indication is in benign prostatic hyperplasia or prostatic cancer, where the use of an antibody against an androgen receptor can alone, or as a conjugate with a therapeutic principle (hormone end-organ antagonist, cytotoxic drug, toxin, or isotope), can decrease the prostatic tissue proliferation.

Where normal organs or tissues are developed abnormally or are displaced in the body, or are insufficiently removed during ablative surgery, the tissue/organ-associated antibodies may be used as tissue-targeted vehicles for delivering therapeutic agents to said tissues in order to induce their involution or chemical and/or isotopic ablation. The antibodies or their fragments (or subfragments) can be conjugated with therapeutic modalities including, but not limited to, isotopes, drugs, toxins, photodynamic therapy agents, cytokines, hormones, autocrines, etc., which are used as cytotoxic or modulating agents, and which have hitherto been employed principally as toxic conjugates to cancer-targeting antibodies, as described in the reviews by Waldmann, T. A., Science 252:1657, 1991; Koppel, G. A., Bioconjug. Chem. 1:13, 1990; Oeltmann, T. N., and Frankel, A. E., FASEB J. 5:2334, 1991; and van den Bergh, H. E., Chemistry in Britain, May 1986, 430–439, incorporated herein in their entirety by reference.

Another therapeutic application for such organ- and tissue-targeting antibodies conjugated with a toxic agent is for the ablation of certain normal cells and tissues as part of another therapeutic strategy, such as in bone marrow ablation with antibodies against bone marrow cells of particular stages of development and differentiation, and in the cytotoxic ablation of the spleen in patients with lymphoma or certain immune diseases, such as immune thrombocytopenic purpura, etc.

Another therapeutic application for such organ- and tissue-targeting antibodies or fragments is to conjugate them with a cytoprotective agent. The conjugate is administered to a patient undergoing chemotherapy or radiation therapy so that the targeted normal organs and tissues are protected during the therapy.

Several methods are known to those skilled in the art for producing organ or tissue associated or specific antibodies, if existing antibodies are considered unsuitable or if different or more discriminating specificities are desired. Generally, whole cells, tissue samples and/or cell or tissue fractions, membranes, antigen extracts or purified antigens are used to challenge the immune system of a suitable animal, e.g., a mouse, rabbit, hamster, goat or the like, the antigen being rendered immunogenic by aggregation if necessary and/or by coadministration with a suitable conventional adjuvant. Hyperimmune antiserum can be isolated and polyclonal antibodies prepared by conventional procedures. Alternatively, spleen cells can be fused with immortal myeloma cells to form hybridoma cells producing monoclonal antibodies, by what are now conventional procedures. See, e.g., the procedures in the above-referenced U.S. Pat. Application Ser. No. 609,607 for illustrative techniques. Hybridomas using animal, e.g., mouse, or human myeloma cell lines and animal or human spleen or lymph cells are all know in the art, and can be made and used for the present method. See, for example, Glassy et al., "Human Monoclonal Antibodies to Human Cancers", in "Monoclonal Antibodies and Cancer", Boss et al., Eds., 163–170 (Academic Press, 1983). The specific antisera or monoclonals are screened for specificity by methods used to screen the anti-lymphocyte clones in the references cited hereinabove, which methods are also conventional by now in this art.

Organ-associated and organ-specific antibodies can be developed by immunizing a suitable animal host with certain mammalian tumors or normal organ/tissue extracts and/or cells, as well as with purified hormone receptors or growth factor receptors. It is well known that use of tumors as immunogens can result in antibodies which not only react with neoplasia but also with normal tissue components which sometimes show an organ-restricted nature. Histogenetic and functional differences between various tissues and organs of the body of course suggest that distinct antigens are present and identifiable. A body of scientific literature already exists which claims the identification of organ-specific antigens, either using classical immunization approaches or by immunizing with specific tumors, and this is reviewed by Goldenberg et al., Cancer Res ., 3455 (1976), showing that such antigens are known and available.

Similar organ- and tissue-associated and specific antigens are identifiable by hybridoma methods which produce monoclonal antibodies. One recent development is the production of human hybridoma monoclonal antibodies by securing lymphocytes or plasma cells from patients showing certain organ-restricted autoimmune diseases, e.g., thyroiditis, gastritis, ulcerative colitis, myositis, and the like. These antibody-producing cells are then fused in vitro with human or murine myeloma cells and hybridomas of appropriate anti-organ and anti-tissue antibody formation are produced and propagated, using well known methods. Also, patients with specific tumor types can be used as a source of such lymphocytes or plasma cells, or such patients can be further immunized with such tumor cells for stimulating the production of anti-organ and anti-tissue antibodies. The lymphatic tissue removed is then used for fusion with suitable myeloma cells, by procedures which are by now well known and conventional in the art.

Organ-associated and organ-specific antigens can be isolated for immunization of another species, e.g., subhuman primates, rodents, rabbits, goats, etc., by a number of methods known in the art, such as isolation of cell membranes or disruption of the cells, e.g., by centrifugation, sonication, etc., to obtain intracellular antigens. It is preferable, for these purposes, to use intracellular as opposed to surface and extracellular antigens. In this manner, organ-associated and organ-specific antigens can be obtained from a large number of tissues and organs of the body, including brain, thyroid, parathyroid, larynx, salivary glands, esophagus, bronchus and lungs, heart, liver, pancreas, stomach and intestines, kidney, adrenal gland, ovary, testis, uterus, prostate, etc. Of further interest is the differentiation of different tissue and cellular components within an organ, such as tubular and glomerular kidney, different regions and cell types of the brain, endocrine and exocrine pancreas, etc., especially by the identification of antigens and antigen epitopes restricted to the individual cell and tissue types in question, as accomplished with polyclonal and/or hybridoma-monoclonal antibody-production methods known in the art.

Antibodies can be produced using cells isolated from tissue obtained at autopsy. For example, mice can be immunized with such tissues for a period necessary to evoke anti-specific organ or tissue antibodies. The spleens of these mice are removed and then fused, by standard methods, with a murine myeloma cell line suitable for hybridoma production. Using methods already standard in the art, monoclonal antibody-producing hybridomas are selected and propagated, and those with organ- or tissue-associated antibody production are cloned and expanded as a source of organ or tissue antibodies. Absolute tissue specificity is not required since significant quantitative differences ordinarily suffice for operational specificity for imaging purposes.

Antibodies and fragments useful in the methods of the present invention include those against antigens associated or produced by normal organs, tissues, and cells, and may or may not be cross-reactive with certain neoplastic tissues.

Preferred are those which, prior to being labeled or conjugated, have a specific immunoreactivity to targeted cells, tissue or organs of at least 60 % and a cross-reactivity to other antigens of less than 35 %.

Specific examples include antibodies and fragments against bone marrow cells, particularly hematopoietic progenitor cells, pancreatic islet cells, spleen cells, parathyroid cells, uterine endometrium, ovary cells, testicular cells, thymus cells, B-cells, T-cells, Null cells, vascular endothelial cells, bile duct cells, gall bladder cells, prostate cells, hormone receptors such as of FSH, LH, TSH, growth factor receptors, such as of epidermal growth factor, urinary bladder cells, and vas deferens cells.

An example of a monoclonal antibody that reacts with granulocytes and which targets to bone marrow cells is NP-2, disclosed in Sharkey et al., Cancer Res. 50:2823–283 (1990). This antibody is useful, when conjugated with a cytotoxic agent, for ablating the bone marrow. Another granulocyte antibody, MN3, has similar properties. Other antibodies that react with other bone marrow cells, especially progenitor cell types, commercially available, are likewise suitable for bone marrow ablation.

Antibodies that target the spleen well include the LL2 (also known as EPB-2) monoclonal antibody, disclosed in Pawlak-Byczkowska, Cancer Research, 49:4568–4577 (1989), which is directed against normal and malignant B-cells, and which can be used for treating normal spleen cells in patients with immune diseases, lymphoma, and other diseases.

Antibodies specific to uterine endometrium are preferred for targeting and therapy of endometriosis, when conjugated with suitable diagnostic or therapeutic agents, respectively.

Antibodies useful in the present invention may be whole immunoglobulin of any class, e.g., IgG, IgM, IgA, IgD, IgE, chimeric or hybrid antibodies with dual or multiple antigen or epitope specificities. It can be a polyclonal antibody, preferably an affinity-purified antibody from a human or an appropriate animal, e.g., a primate, goat, rabbit, mouse or the like. Monoclonal antibodies are also suitable for use in the present method, and are preferred because of their high specificities. They are readily prepared by what are now considered conventional procedures of immunization of mammals with immunogenic antigen preparation, fusion of immune lymph or spleen cells with an immortal myeloma cell line, and isolation of specific hybridoma clones. More unconventional methods of preparing monoclonals antibodies are not excluded, such as interspecies fusions and genetic engineering manipulations of hypervariable regions, since it is primarily the antigen specificity of the antibodies that affects their utility in the present invention. It will be appreciated that newer techniques for production of monoclonals can also be used, e.g., human monoclonals, interspecies monoclonals, chimeric (e.g., human/mouse) monoclonals, genetically engineered antibodies and the like.

Antibody fragments useful in the present invention are $F(ab')_2$, $F(ab)_2$, Fab', Fab, Fv and the like, including hybrid fragments. Also useful are any subfragments retaining the hypervariable, antigen-binding region of an immunoglobulin and having a size smaller than a Fab' fragment. This will include genetically engineered and/or recombinant proteins, whether, single-chain or multiple-chain, which incorporate an antigen binding site and otherwise function in vivo as targeting vehicles in substantially the same way as natural immunoglobulin fragments. Such single-chain binding molecules are disclosed in U.S. Pat. No. 4,946,778, which is hereby incorporated by reference. Fab' antibody fragments may be conveniently made by reductive cleavage of $F(ab')_2$ fragments, which themselves may be made by pepsin digestion of intact immunoglobulin. Fab antibody fragments may be made by papain digestion of intact immunoglobin, under reducing conditions, or by cleavage of $F(ab)_2$ fragments which result from careful papain digestion of whole Ig. The fragments may also be produced by genetic engineering.

It should be noted that mixtures of antibodies, isotopes, and immunoglobulin classes can be used, as can hybrid antibodies. The hybrids can have two different antigen specificities, e.g., one arm binding to one organ antigen and another arm binding to another antigen, or one arm could bind to one epitope on the antigen, and the other arm could bind to another epitope. The foregoing are merely illustrative, and other combinations of specificities can be envisioned that also fall within the scope of the invention.

Hybrid antibody fragments with dual specificities can be prepared analogously to the anti-tumor marker hybrids disclosed in U.S. Pat. No. 4,361,544. Other techniques for preparing hybrid antibodies are disclosed in, e.g., U.S. Pat. No. 4,474,893, U.S. Pat. No. 4,479,895, U.S. Pat. No. 4,714,681, U.S. Pat. No. 4,474,893 and in Milstein et al., *Immunol. Today*, 5,299 (1984), all incorporated herein by reference.

The methods of the present invention include the use of pretargeted antibody methods, and the use of light with porphyrins and fluorescent dyes. The methods taught in the prior art are utilized in cancer therapy. However, if the antibody fragment utilized is targeted to organs and tissues specified herein, analogous procedures may be used in the present invention.

For example, Paganelli, Nucl. Med. Commun. 12:211, 1991, incorporated herein in its entirety by reference, disclosed antibody pretargeting procedures, such as using streptavidin-conjugated antibodies, biotinylated antibodies in conjunction with avidin and biotin, bifunctional antibodies, antibody-hapten complexes, and enzyme-conjugated antibodies, in addition to delivering radiation to target cells and tissues by such 2- and 3-step procedures.

When the cell or tissue is pretargeted by a 2- or 3-step procedure, the subject is injected with a first composition comprising, for example, a streptavidin-conjugated antibody, biotinylated antibody to be used in conjunction with avidin and biotin, bifunctional antibody, antibody-hapten complexes, or enzyme-conjugated antibody, wherein the antibody is an antibody or antibody fragment which specifically binds a marker produced by or associated with said cell or tissue. After the first composition accretes at the targeted tissue or cell, a second composition, which bears the desired imaging, therapeutic, cytoprotective or activating principle, is administered. The second composition either activates the first composition or couples with the first composition to produce a desired effect.

When the cell or tissue is pretargeted in a 3-step procedure, the subject is injected with the first composition which comprises biotinylated antibody or fragment, is then injected with a clearing composition comprising an agent to clear circulating biotinylated antibody or fragment, and then injected with the second composition which comprises biotin conjugated with the desired imaging, therapeutic, cytoprotective or activating agent.

When the term "antibody" is used herein, all the above types of antibodies and fragments are included therein.

The use of light and porphyrins in cancer therapy has been reviewed by van den Bergh (Chemistry in Britain, May 1986, Vol. 22, pp. 430–437), which is incorporated herein in its entirety reference, and includes reference to the use of monoclonal antibodies conjugated with a photosensitizer for transporting the latter to the tumor. This has been suggested earlier by Oseroff in Photochem. Photobiol. 41:35S, 1985; Mew et al., Cancer Res. 45:4380, 1985; Hasan et al., Immunity to Cancer, II, pp. 471–477, 1989 [Alan R. Liss, Inc. publishers]; and Pelegrin et al., Cancer 67:2529, 1991 [all incorporated herein by reference], which involved tissue culture or animal studies of fluorescent dyes attached to antitumor antibodies.

Radiolabeled antibodies to markers characteristic of hypoplastic, absent, displaced or ectopic tissues or organs are a new kind of agent. They are an example of an immunologic, organ-specific imaging agent which can be used to ascertain the location and shape of a specific organ and reveal possible abnormalities therein. Such agents are useful for imaging organs such as, e.g., liver, spleen, pancreas, and the like, and many antibodies which specifically bind to tissues of these organs are known and/or under current investigation and development.

Among the radioisotopes used, gamma-emitters, positron-emitters, x-ray emitters and fluorescence-emitters are suitable for localization and/or therapy, while beta-emitters and alpha-emitters may also be used for therapy. Suitable radio-isotopes for the methods of the present invention include: Astatine-211, Iodine-123, Iodine-125, Iodine-126, Iodine-131, Iodine-133, Bismuth-212, Bromine-77, Indium-111, Indium-113m, Gallium-67, Gallium-68, Ruthenium-95, Ruthenium-97, Ruthenium-103, Ruthenium-105, Mercury-107, Mercury-203, Rhenium-186, Rhenium-188, Tellurium-121m, Tellurium-122m, Tellurium-125m, Thulium-165, Thulium-167, Thulium-168, Technetium-99m, Fluorine-18, Silver-111, Platinum-197, Palladium-109, Copper-67, Phosphorus-32, Phosphorus-33, Yttrium-90, Scandium-47, Samarium-153, Lutetium-177, Rhodium-105, Praseodymium-142, Praseodymium-143, Terbium-161, Holmium-166, Gold-199, Cobalt-57, Cobalt-58, Chromium-51, Iron-59, Selenium-75, Thallium-201, and Ytterbium-169. Preferably the radioisotope will emit in the 10–5,000 kev range, more preferably 50–1,500 kev, most preferably 50–500 kev.

Isotopes preferred for diagnostic use include Iodine-123, Iodine-131, Indium-111, Gallium-67, Ruthenium-97, Technetium-99m, Copper-67, Cobalt-57, Cobalt-58, Chromium-51, Iron-59, Selenium-75, Thallium-201, and Ytterbium-169.

Isotopes preferred for therapeutic use include: Iodine-125, Iodine-131, Rhenium-186, Rhenium-188, Silver-111, Platinum-197, Palladium-109, Copper-67, Phosphorus-32, Phosphorus-33, Yttrium-90, Scandium-47, Samarium-153, Lutetium-177, Rhodium-105, Praseodymium-142, Praseodymium-143, Terbium-161, Holmium-166, and Gold-199.

Many drugs and toxins are known which have cytotoxic effects on cells. They are to be found in compendia of drugs and toxins, such as the Merck Index, Goodman and Gilman, and the like, and in the references cited above. Any such drug can be conjugated to or loaded onto the antibody by conventional means well know in the art, and illustrated by analogy to those described above.

The present invention also contemplates dyes used, for example, in photodynamic therapy, conjugated to the antibodies and fragments, and used in conjunction with appropriate nonionizing radiation.

Examples of known cytotoxic agents useful in the present invention are listed in Goodman et al., "The Pharmacological Basis of Therapeutics," Sixth Edition, A. G. Gilman et al, eds./ Macmillan Publishing Co. N.Y., 1980. These include taxol, nitrogen mustards, such as, mechlorethamine, cyclophosphamide, melphalan, uracil mustard and chlorambucil; ethylenimine derivatives, such as, thiotepa; alkyl sulfonates, such as, busulfan; nitrosoureas, such as, carmustine, lomustine, semustine and streptozocin; triazenes, such as, dacarbazine; folic acid analogs, such as, methotrexate; pyrimidine analogs, such as, fluorouracil, cytarabine and azaribine; purine analogs, such as, mercaptopurine and thioguanine; vinca alkaloids, such as, vinblastine and vincristine; antibiotics, such as, dactinomycin, daunorubicin, doxorubicin, bleomycin, mithramycin and mitomycin; enzymes, such as, L-asparaginase; platinum coordination complexes, such as, cisplatin; substituted urea, such as hydroxyurea; methyl hydrazine derivatives, such as, procarbazine; adrenocortical suppressants, such as, mitotane; hormones and antagonists, such as, adrenocortisteroids (prednisone), progestins (hydroxyprogesterone caproate, medroprogesterone acetate and megestrol acetate), estrogens (diethylstilbestrol and ethinyl estradiol), antiestrogens (tamoxifen), and androgens (testosterone propionate and fluoxymesterone).

The antibodies and fragments of the invention may be radiolabeled by a variety of methods known in the art. Many of these methods are disclosed in the above-referenced U.S. Patents and Patent Applications, and include direct radioiodination. See also, Rayudu, op. cit.; and Childs et al., *J. Nuc. Med.*, 26, 293 (1985). Any conventional method of radiolabeling which is suitable for labeling isotopes for in vivo use will be generally suitable for labeling imaging agents according to the present invention.

The antibodies and fragments may be conjugated to therapeutic agents such as drugs, toxins, boron addends, isotopes, fluorescent dyes activated by nonionizing radiation, hormones, autocrines, cytokines, cytoprotective agents, etc., by methods known to those skilled in the art. U.S. Pat. No. 5,057,313, Shih et al, hereby incorporated by reference, teaches one such method.

Loading of drugs on to a carrier as disclosed in U.S. Pat. No. 5,057,313 will depend upon the potency of the drug, the efficiency of the antibody targeting and the efficacy of the conjugate once it reaches its target. In most cases, it is desirable to load at least 20, preferably 50 and often 100 or more molecules of a drug on a carrier. The ability to partially or completely detoxify a drug as a conjugate, while it is circulation, can reduce systemic side effects of the drug and permit its use when systemic administration of the unconjugated drug would be unacceptable.

Toxins will often be less heavily loaded than drugs, but it will still be advantageous to load at least 1, preferably 5 and in some cases 10 or more molecules of toxin on a carrier and load at least one carrier chain on the antibody for targeted delivery.

The conjugate will generally be administered as a sterile aqueous solution in phosphate-buffered saline. Dosage will depend on the therapeutic utilized, the desired effect and the side effects experienced by the patient.

The imaging agent will normally be administered at a site and by a means that insure that it is mobilized and taken up into the organ or tissue which will vary by the tissue or organ to be imaged.

The agent is preferable injected by a systemic route, e.g., intravenously, intraarterially, intramuscularly or subcutaneously, or by a combination of systemic routes insuring its accretion in the tissue or organ of interest.

Volumes of labeled antibody imaging agent, normally in sterile physiological saline, will normally vary somewhat depending upon the site, the concentration, and the number of injections. Activity of the agent will normally be in the range of about 10–40, preferably about 15–25 mCi per injection for a Tc-99m-labeled agent. It will be appreciated that the activity will vary for other radioisotopes, depending upon their half-lives, their imaging characteristics, i.e., energy ranges, emission intensities, scatter and the like, the stability of the labeled agent, especially antibody conjugates, their distribution and clearance, and the time at which imaging is to be done. Adjustment of these parameters will be conventional for the ordinary skilled clinician.

Imaging is normally effected up to about 24 hours, more preferably at about 2–6 or less hours after injection of the imaging agent, to obtain the "positive" image of the organ or tissue. Two- and three-step targeting methods will require longer periods.

Timing of injections of imaging agents will depend upon the types of agents and methods used and the targeting patterns to the organs and tissues of interest.

The conjugate will generally be administered as a sterile aqueous solution in a buffered saline. Dosage units of about 1–200 mg of conjugate will be administered for a duration of treatment as determined by the skilled practitioner. It may be necessary to reduce the dosage and/or use antibodies from other species and/or hypoallergenic antibodies, e.g., chimeric mouse/human, CDR-grafted ("humanized"), or primate antibodies, to reduce patient sensitivity.

Routes of administration include intravenous, intraarterial, intrapleural, intraperitoneal, intrathecal, subcutaneous or by perfusion.

An application of the organ- or tissue-specific or organor tissue-associated antibodies disclosed hereinabove is for normal organ scintigraphy and magnetic resonance imaging (mri). In this case, a suitably radiolabeled antibody/fragment or an antibody/fragment bearing a mr image enhancing agent is administered with the intention of obtaining a "positive" image of the organ, when normal, and a defect in organ visualization if pathology is present. This provides a new approach to organ- and tissue-specific nuclear and magnetic resonance imaging of organs and tissues in the body, based upon their immunological specificity.

The method of the invention can be practiced either with scintigraphic or magnetic resonance imaging agents. A combination of these imaging agents can also be used, although this requires more complex instrumentation and data processing.

Scintigraphic imaging according to the method of the invention is effected by obtaining a scintigram of the tissue or organ of interest, using as an imaging agent a radiolabeled antibody which specifically binds to a marker produced by or associated with the tissue or organ or at a locus proximal to the tissue or organ and draining into the structure, such that the antigen/marker accretes in discrete foci therein.

The scintigram is normally taken by a gamma imaging camera having one or more windows for detection of energies in the 50–500 keV range. Use of radioisotopes with higher energy, beta, or positron emissions would entail use of imaging cameras with the appropriate detectors, all of which are conventional in the art.

The scintigraphic data can be stored in a computer for later processing.

Magnetic resonance imaging (mri) is effected in an analogous manner to scintigraphic imaging except that the imaging agents will contain magnetic resonance (mr) enhancing species rather than radioisotopes. It will be appreciated that the magnetic resonance phenomenon operates on a different principle from scintigraphy. Normally, the signal generated is correlated with the relaxation times of the magnetic moments of protons in the nuclei of the hydrogen atoms of water molecules in the region to be imaged. The magnetic resonance image enhancing agent acts by increasing the rate of relaxation, thereby increasing the contrast between water molecules in the region where the imaging agent accretes and water molecules elsewhere in the body. However, the effect of the agent is to decrease both $T_1$ and $T_2$, the former resulting in greater contrast while the latter results in lesser contrast. Accordingly, the phenomenon is concentration-dependent, and there is normally an optimum concentration of a paramagnetic species for maximum efficacy. This optimal concentration will vary with the particular agent used, the locus of imaging, the mode of imaging, i.e., spin-echo, saturation-recovery, inversion-recovery and/or various other strongly $T_1$-dependent or $T_2$-dependent imaging techniques, and the composition of the medium in which the agent is dissolved or suspended. These factors, and their relative importance are known in the art. See, e.g., Pykett, *Scientific American*, 246, 78(1982); Runge et al., *Am. J. Radiol.*, 141, 1209(1983).

The mr image enhancing agent must be present in sufficient amounts to enable detection by an external camera, using magnetic field strengths which are reasonably attainable and compatible with patient safety and instrumental design. The requirements for such agents are well known in the art for those agents which have their effect upon water molecules in the medium, and are disclosed, inter alia, in Pykett, op. cit., and Runge et al., op. cit.

Preparation of antibodies conjugated to a magnetic resonance image enhancing agent can be effected by a variety of methods. In order to load an antibody molecule with a large number of paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and the like groups known to be useful for this purpose. The chelate is normally linked to the antibody by a group which enables formation of a bond to the antibody with minimal loss of immunoreactivity and minimal aggregation and/or internal cross-linking. Other, more unusual, methods and reagents for conjugating chelates to antibodies are disclosed in copending U.S. Pat. Application Ser. No. 742,436 to Hawthorne, entitled "Antibody Conjugates", filed Jun. 7, 1985, the disclosure of which is incorporated herein in its entirety by reference.

MRI contrast agents are well known in the art and include, for example, Gadolinium, Iron, Manganese, Rhenium, Europium, Lanthanium, Holmium, and Ferbium.

The mr scans are stored in a computer and the images processed analogously to the scintigraphic data.

Several agents are known to those skilled in the art which protect normal cells, tissues and organs during treatment of cancer with radiation and cytotoxic agents. Such agents are disclosed in "Cancer Chemotherapy—Principles & Practice", Chabner et al. eds., J. B. Lippincott Company, Philadelphia, 1990, especially Chapter 18, "Radiation and Chemotherapy Sensitizers and Protectors" by Coleman et al., which is incorporated herein by reference.

These agents include WR-2721 (S2-[3-aminopropylamino]ethylphosphorothioic acid), known as Ethyol being developed by U.S. Bioscience, WR-2721's dephosphorylated metabolite, WR-1065, and MGI 136 being developed by MGI Pharma Inc.

The reagents are conveniently provided in kit form, adapted for use in the methods of the invention. Kits will normally contain separate sealed sterile vials of injectable solutions of labeled reagents, or lyophilized antibodies/ fragments or antibody/fragment conjugates and vials of sterile conventional injection vehicles with which they will be mixed just prior to administration.

Kits may also include reagents for labeling antibodies, e.g., Chloramine-T (for I-131 or I-123 labeling), $SnCl_2$ (for Tc-99m labeling using pertechnetate from a commercial generator), short columns for sizing and/or purification of reagents, and other conventional accessory materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in Celsius; unless otherwise indicated, all parts and percentages are by weight.

EXAMPLES

Example 1—Imaging Pancreatic Cells

Hybridoma-monoclonal antibodies are made in the mouse to the Langerhans cells of the endocrine pancreas, derived from a human autopsy specimum shortly after death. The monoclonal F(ab')$_2$ reactive against the antigen epitope showing relatively high specificity for Langerhans cells of the pancreas, as demonstrated, e.g., by immunohistology, are labeled with a gamma-emitting isotope, such as with I-123, and injected, e.g. 0.15 mg monoclonal against endocrine pancreas antigen, labeled using Chloramine-T with I-123, at a dose of 3.0 mCi, injected i.v. in a 3-month-old male suspected of having pathology of the endocrine pancreas. External gamma-camera imaging is performed at 6, 24, and 48 hours after injection, without substraction. In this specific case, decreased to almost absent accretion of I-123 radioactivity in the pancreas is suggestive of endocrine pancreas pathology in an infant presenting with pancreas hormone deficiency shortly after birth.

Example 2—Bone Marrow Ablation and Cancer Therapy

A middle-age woman with advanced breast cancer, including bone and bone marrow invasion, has an aliquot of her bone marrow removed and harvested for regrafting after clearing the marrow of the cancer cells in vitro. The bone marrow in the patient is then destroyed by i.v. infusion of 20 mg NP-2 monoclonal antibody F(ab')$_2$ labeled with 200 mCi Rhenium-188 according to the method of Griffiths et al. (Cancer Res. 51:4594, 1991). Approximately 3 weeks later, there is evidence of severe bone marrow toxicity which requires the infusion of the autologous bone marrow which was previously cleared of cancer cells, in combination with hematopoietic growth factor administration, in this case with GM-CSF given repeatedly before and after marrow grafting. Six weeks later, the patient has renewed bone marrow function and an MN3-Fab' (Tc-99m) bone marrow scan shows good bone marrow imaging without evidence of metastatic defects. She is now a candidate for treatment of other sites of her metastatic breast cancer.

Example 3—Endometriosis Detection

A woman complains of amenorrhea and infertility and is suspected of having endometriosis. She is injected with 1 mg of anti-endometrial tissue monoclonal antibody Fab' labeled with Tc-99m (20 mCi) intravenously. Four hours later, a total body planar scan reveals abnormal foci of radioactivity in the right lower chest and in the retroperitoneum, which are confirmed by single photon emission computer tomography immediately thereafter. The patient is then referred to ablation therapy.

Example 4—Endometriosis Therapy

A woman is diagnosed to have endometriosis and is referred to her gynecologist for treatment. An endometrial tissue-associated monoclonal antibody IgG and a monoclonal antibody IgG against FSH receptor are labeled with I-131 by the chloramine-T method at a specific activity of 10 mCi/mg, and the combination is then infused i.v. to deliver a dose of 100 mCi I-131. After monitoring her peripheral blood cells during the next month, a repeat therapy is given 6 weeks later. After an additional 6 weeks, the patient shows a complete remission of her symptoms.

The preceding examples can be repeated with similar success by substituting the generically or specifically described reactants and/or operating conditions of this invention for those used in the preceding examples.

It will be understood that the invention is not limited to use of known antibodies or markers, but can be practiced with antibodies to any marker produced by or associated with an organ or tissue.

From the foregoing description, one skilled in the art can easily ascertain the essential characteristics of this invention and, without departing from the spirit and scope thereof, can make various changes and modifications of the invention to adapt it to various usages and conditions.

I claim:

1. A method of imaging hypoplastic, anatomically displaced or ectopic cells or tissues in a mammalian subject by scintigraphic or magnetic resonance imaging, comprising the steps of: (a) parenterally injecting a mammalian subject, at a locus and by a route providing access to an organ of interest, with an antibody or antibody fragment which specifically binds a marker produced by or associated with said cell or tissue, said antibody or antibody fragment being labeled with a radioisotope or with a magnetic resonance image enhancing agent capable of external detection, the amount of the labeled antibody or antibody fragment being sufficient to permit a scintigraphic image or an enhanced magnetic resonance image of said organ to be obtained; and (b) obtaining a positive scintigraphic image or positive enhanced magnetic resonance image of said organ, at a time after injection of said agent sufficient for said agent to diffusely accrete in said organ and specifically bind to said marker.

2. The method of claim 1, wherein said imaging is used in diagnosis of DiGeorge's syndrome.

3. The method of claim 1 wherein the isotope emits at 50–1,500 kev energy.

4. The method of claim 1 wherein the mri enhancing agent is a species of Gadolinium, Iron, Manganese, Rhenium, Europium, Lanthanium, Holmium, or Ferbium.

5. The method of claim 1, wherein said imaging is used in diagnosis of thymic aplasia or agenesis.

6. The method of claim 1 wherein the antibody is a Fv, single chain antibody, Fab, Fab', or F(ab')$_2$ fragment or intact antibody.

7. The method of claim 1 wherein the antibody or fragment has a specific immunoreactivity to targeted cells or tissues of at least 60 % and a cross-reactivity to other antigens of less than 35 %.

8. The method of claim 1, wherein said cells or tissues to be imaged are hypoplastic cells or tissues.

9. The method of claim 1, wherein said cells or tissues to be imaged are anatomically displaced cells or tissues.

10. The method of claim 1, wherein said cells or tissues to be imaged are ectopic cells or tissues.

11. The method of claim 10, wherein said cells or tissues to be imaged are endometrial tissues.

12. The method of claim 1, wherein said imaging is used in diagnosis of juvenile diabetes.

13. The method of claim 1 wherein the cell or tissue is pretargeted with a first composition comprising a streptavidin-conjugated antibody, biotinylated antibody to be used in conjunction with avidin and biotin, bifunctional antibody, antibody-hapten complexes, or enzyme-conjugated antibody, wherein the antibody is an antibody or antibody fragment which specifically binds a marker produced by or associated with said cell or tissue, and after the first composition accretes at the targeted tissue or cell, a second composition, which bears the imaging principle, is administered which activates the first composition or couples with the first composition to produce a desired effect.

14. The method of claim 13, wherein the cell or tissue is pretargeted by injecting the subject with the first composition which comprises biotinylated antibody or fragment, optionally injecting the patient with a clearing composition comprising an agent to clear circulating biotinylated antibody or fragment, and then injecting the second composition which comprises biotin conjugated with isotope or mri enhancing agent.

* * * * *